United States Patent

Antaki et al.

[11] Patent Number: 5,537,335
[45] Date of Patent: Jul. 16, 1996

[54] FLUID DELIVERY APPARATUS AND ASSOCIATED METHOD

[75] Inventors: James F. Antaki, Allison Park; Robert F. Labadie; Harvey S. Borovetz, both of Pittsburgh, all of Pa.

[73] Assignee: University of Pittsburgh of the Commonwealth System of Higher Education, Pittsburgh, Pa.

[21] Appl. No.: 554,109

[22] Filed: Nov. 6, 1995

Related U.S. Application Data

[63] Continuation of Ser. No. 146,501, Nov. 1, 1993.
[51] Int. Cl.⁶ .................................................. A61B 5/0235
[52] U.S. Cl. .................................. 364/510; 623/3; 137/7
[58] Field of Search ........................ 364/510 B, 188, 364/571.01; 128/10,637, 680; 134/570; 210/136; 623/3; 137/7, 14, 82

[56] References Cited

U.S. PATENT DOCUMENTS

| | | | |
|---|---|---|---|
| Re. 30,317 | 7/1980 | Lübbers et al. | 128/635 |
| 3,639,084 | 2/1972 | Goldhaber | 417/394 |
| 3,741,208 | 6/1973 | Jonsson et al. | 128/145.6 |
| 3,864,248 | 2/1975 | Granger et al. | 210/19 |
| 4,052,971 | 10/1977 | Salzgeber et al. | 123/139 |
| 4,250,908 | 2/1981 | Velie | 137/7 |
| 4,459,977 | 7/1984 | Pizon et al. | 128/1 |
| 4,588,404 | 5/1986 | Lapeyre | 623/3 |
| 4,734,092 | 3/1988 | Millerd | 604/67 |
| 4,739,771 | 4/1988 | Manwaring | 128/691 |
| 4,858,615 | 8/1989 | Meinema | 128/668 |
| 4,859,078 | 8/1989 | Bowman et al. | 374/47 |
| 4,961,441 | 10/1990 | Salter | 137/14 |
| 4,971,016 | 11/1990 | Peters et al. | 123/500 |
| 5,050,613 | 9/1991 | Newman et al. | 128/670 |
| 5,098,370 | 3/1992 | Rahat et al. | 600/16 |
| 5,101,828 | 4/1992 | Welkowitz et al. | 128/668 |
| 5,150,292 | 9/1992 | Hoffmann et al. | 364/413.07 |
| 5,152,297 | 10/1992 | Meister et al. | 128/672 |
| 5,188,604 | 2/1993 | Orth | 604/153 |
| 5,224,484 | 7/1993 | Newell | 128/680 |
| 5,230,362 | 7/1993 | Goodman | 137/489 |
| 5,247,434 | 9/1993 | Peterson et al. | 364/188 |
| 5,282,489 | 2/1994 | Gooch | 137/85 |
| 5,305,745 | 4/1994 | Zacouto | 128/637 |
| 5,313,964 | 5/1994 | Dausch et al. | 134/57 |
| 5,355,890 | 10/1994 | Aguirre et al. | 128/680 |

OTHER PUBLICATIONS

Berceli, S. A. et al., "Mechanisms of vein graft atherosclerosis: LDL metabolism and endothelial action reorganization", *Journal Of Vascular Surgery*, vol. 13, No. 2, Feb. 1991, pp. 336–347.

(List continued on next page.)

*Primary Examiner*—Ellis B. Ramirez
*Assistant Examiner*—Patrick J. Assouad
*Attorney, Agent, or Firm*—David V. Radack; Eckert Seamans Cherin & Mellott

[57] ABSTRACT

A fluid delivery apparatus including a chamber for holding a conduit, such as a portion of a human vascular tissue, a fluid supply source for delivering a fluid into the conduit and a fluid pressure modulating device for modulating the fluid pressure supplied from the fluid source before the fluid enters the conduit. The modulating device produces a fluid having a desired pressure waveform for delivery to the conduit. The modulating device includes a microprocessor that digitizes the desired pressure waveform into a plurality of discrete digitized data points and stores a motion controller computer program. The modulating device further includes a motion controller which receives the digitized data points and the motion controller computer program and which at least partially restricts the delivery of the fluid to the conduit based on the digitized data points and the motion controller computer program to produce the desired pressure waveform for delivery to the conduit. An associated method of delivering a fluid having desired pressure to a conduit is also provided.

15 Claims, 4 Drawing Sheets

OTHER PUBLICATIONS

Brant, A. M. et al., "Simulation in Vitro of Pulsatile Vascular Hemodynamics Using a CAD/CAM–Designed Cam Disc and Roller Follower", *Artif. Organs.*, vol. 10, No. 5, 1986, pp. 419–421.

Brant, A. M. et al., "Measurement in Vitro of pulsatile arterial diameter using a helium—neon laser", *J. Applied Physiology*, vol. 62, 1987, pp. 679–683.

Campeau, L. et al., "The Relation of Risk Factors To The Development Of Atherosclerosis In Saphenous–Vein Bypass Grafts And The Progression Of Disease In The Native Circulation", *The New England Journal of Medicine*, vol. 311, No. 21, Nov. 22, 1984, pp. 1329–1332.

Cushing, G. L. et al., "Quantitation and Localization of Apolipoproteins [a] and B in Coronary Artery Bypass Vein Grafts Resected at Re–operation", *Arteriosclerosis*, vol. 9, No. 5, Sep./Oct. 1989, pp. 593–603.

Grondin, C. M. et al., "Coronary Artery Bypass Grafting With Saphenous Vein", Supplement I–*Circulation*, Vol. 79, No. 6, Jun. 1989, pp. I–24–I–29.

Ligush, John, Jr. et al., "Evaluation of Endothelium–Derived Nitric Oxide Mediated Vasodilation Utilizing *Ex Vivo* Perfusion of an Intact Vessel", *Journal of Surgical Research*, Vol. 52, 1992, pp. 416–421.

Neitzel, G. F. et al., "Atherosclerosis in Aortocoronary Bypass Grafts. Morphologic Study and Risk Factor Analysis 6 to 12 Years After Surgery", *Arteriosclerosis*, vol. 6, No. 6, Nov./Dec. 1986, pp. 594–600.

Ross, R., "The Pathogenesis Of Atherosclerosis–An Update", *The New England Journal of Medicine*, vol. 314, No. 8, Feb. 20, 1986, pp. 488–500.

Schwenke, D. C. et al., "Quantification in Vivo of Increased LDL Content and Rate of LDL Degradation in Normal Rabbit Aorta Occurring at Sites Susceptible to Early Atherosclerotic Lesions", *Circulation Research*, vol. 62, No. 4, Apr. 1988, pp. 699–710.

Schwenke, D. C. et al., "Initiation of Atherosclerotic Lesions in Cholesterol–fed Rabbits. I. Focal Increases in Arterial LDL Concentration Precede Development of Fatty Streak Lesions", *Arteriosclerosis*, vol. 9, No. 6, Nov./Dec. 1989, pp. 895–907.

Schwenke, D. C. et al., "Initiantion of Atherosclerotic Lesions in Cholesterol–fed Rabbits. II. Selective Retention of LDL vs. Selective Increases in LDL Permeability in Susceptible Sites of Arteries", *Arteriosclerosis*, vol. 9, No. 6, Nov./Dec. 1989, pp. 908–918.

Shelton, M. E. et al., "A Comparison of Morphologic and Angiographic Findings in Long–Term Internal Mammary Artery and Saphenous Vein Bypass Grafts", *Journal of American College of Cardiology*, vol. 11, No. 2, Feb. 1988, pp. 297–307.

Walton, K. W. et al., "Atherosclerosis in Vascular Grafts for Peripheral Vascular Disease,. Part 1. Autogenous Vein Grafts", *Atherosclerosis*, vol. 54, 1985, pp. 49–64.

Zwolak, R. M. et al., "Kinetics of vein graft hyperplasia: Association with tangential stress", *Journal of Vascular Surgery*, vol. 5, No. 1, Jan. 1987, pp. 126–136.

Labadie, R. F. et al., "An In–Virto Hemodynamic Replication System to be Used for Exposing Vascular Tissue to Precisely Controlled Hemodynamics", *Proceedings of the American Society of Mechanical Engineers (ASME) 1992 Advances in Bioengineering BED*, vol. 22, pp. 497–500.

FLUID DELIVERY APPARATUS AND ASSOCIATED METHOD

CROSS REFERENCE TO RELATED APPLICATION

This application is a continuation of U.S. patent application Ser. No. 08/146,501, filed Nov. 1, 1993.

BACKGROUND OF THE INVENTION

This invention relates to a fluid delivery apparatus and an associated method and more particularly to a fluid delivery apparatus in which a predetermined pressure waveform is introduced into a conduit, such as a human saphenous vein.

Fluid delivery apparatus which mock the circulation of blood in humans are extremely useful to test various medical devices, such as artificial heart valves. This apparatus is intended for exposing body tissues, such as a vascular tissue, to pulsatile flow. The rationale for this apparatus is the compelling evidence that the saphenous vein used in coronary bypass operations, once implanted in the arterial circulation, develops atherosclerosis (hardening of the arteries) at an accelerated rate. C. M. Grondin et al., "Coronary Artery Bypass Grafting With Saphenous Vein", *Circulation*, Supplement I, Vol. 79, No. 6, June 1989, pp. 1-24-1-29. One of the hypotheses is that because the saphenous vein is exposed to the pressure and flow present in the arterial (versus venous) circulation the subsequent "arterialization" of the saphenous vein may be an important component in the disease process. This hypothesis is, in part, supported by the excellent viability of internal mammary artery grafts (versus saphenous vein grafts) in which atherosclerotic degeneration is generally absent. M. E. Shelton et al., "A Comparison of Morphologic and Angiographic Findings in Long-Term Internal Mammary Artery and Saphenous Vein Bypass Grafts", *J. Am. College of Cardiology*, Vol. 11, No. 2, February 1988, pp. 297–307.

What is needed, therefore, is a fluid delivery apparatus in which pressure waveforms, which mimic the pressure waveforms of the human circulation system, are produced, so that the effects of "arterialization" can be studied. Furthermore, the fluid delivery apparatus can be used to "arterialize" vascular tissue so as to condition it for use in bypass surgery. These needs would be fulfilled by a precisely controlled fluid delivery apparatus that can effectively mimic the fluid pressure waveforms found in a human circulatory system.

In addition to the use of the fluid delivery apparatus for arterialization studies, many pharmaceutical manufacturers desire to test the effects of certain drugs on vascular tissue under conditions similar to those which are found in the human circulatory system. Presently, static tissue cultures are used for this purpose, or actual human trials are initiated. A fluid delivery apparatus would provide a more realistic test than the static culture tests yet safer then human trials. Also, using the fluid delivery apparatus would provide the researcher a way to isolate the effects of hemodynamic variables (such as pressure, flow and heart rate) on the vascular tissue. A fluid delivery apparatus in which predetermined and controlled pressure waveforms are produced is also needed for this application.

As can be seen, there is a need for a fluid delivery system that efficiently and precisely controls the pressure waveform that is introduced into a conduit, such as a human saphenous vein.

SUMMARY OF THE INVENTION

The fluid delivery apparatus of the invention has met the above-described need. The fluid delivery apparatus includes a chamber for holding a conduit, such as a portion of a human saphenous vein, a fluid supply source for delivering a fluid into the conduit and a fluid pressure modulating device for modulating the fluid pressure supplied from the fluid source before the fluid enters the conduit. The modulating device produces a fluid having a desired pressure waveform for delivery to the conduit. The modulating device includes a microprocessor that digitizes the desired pressure waveform into a plurality of discrete digitized data points and stores a motion controller computer program used in generating the desired pressure waveform. The modulating device further includes a motion controller which receives the digitized data points and the motion controller computer program and which at least partially restricts the delivery of fluid to the conduit based on the digitized data points and the motion controller computer program to produce the desired pressure waveform for delivery to the conduit.

A method of delivering fluid having a desired pressure to a conduit is also provided. The method includes providing a chamber to hold the conduit and a fluid supply means for delivering fluid to the conduit and modulating the pressure of the fluid before the fluid is delivered to the conduit so that the fluid has a desired pressure. The modulating step comprises at least partially restricting the delivery of the fluid to the conduit, measuring the pressure of the fluid prior to the fluid entering into the conduit, comparing the measured pressure of the fluid to the desired pressure and adjusting the restriction of the delivery of the fluid to the conduit based on the comparison.

It is an object of the invention to deliver to a conduit a fluid flow having a desired pressure waveform.

It is a further object of the invention to provide a fluid delivery apparatus that can mimic the circulation system of a human.

It is yet a further object of the invention to provide a motion controller apparatus that can modulate a steady pressure and fluid flow to produce a desired pressure waveform and fluid flow.

It is still another object of the invention to provide a computer-based method of modulating a pressure waveform that is based on an "adaptive learning" technique.

It is yet another object of the invention to provide a mechanical fluid flow occluder that is controlled by a microprocessor.

These and other objects of the invention will be fully understood from the following description of the invention with reference to the drawings appended to this application.

DETAILED DESCRIPTION

The fluid delivery apparatus of the invention is useful whenever it is desired to introduce a fluid flow having a desired pressure waveform into a conduit. FIGS. 1–6 illustrate one embodiment of the invention. The fluid delivery apparatus 10 shown in these figures is used to perfuse a blood vessel. It will be appreciated, however, that the invention is not limited to this use and other biological uses of the apparatus 10, such as testing the effects of pharmaceuticals on vascular tissue or non-biological uses such as providing a desired fluid pressure and flow (either steady or pulsatile) in a pipe or other conduit are also contemplated by the invention.

Figure 1:
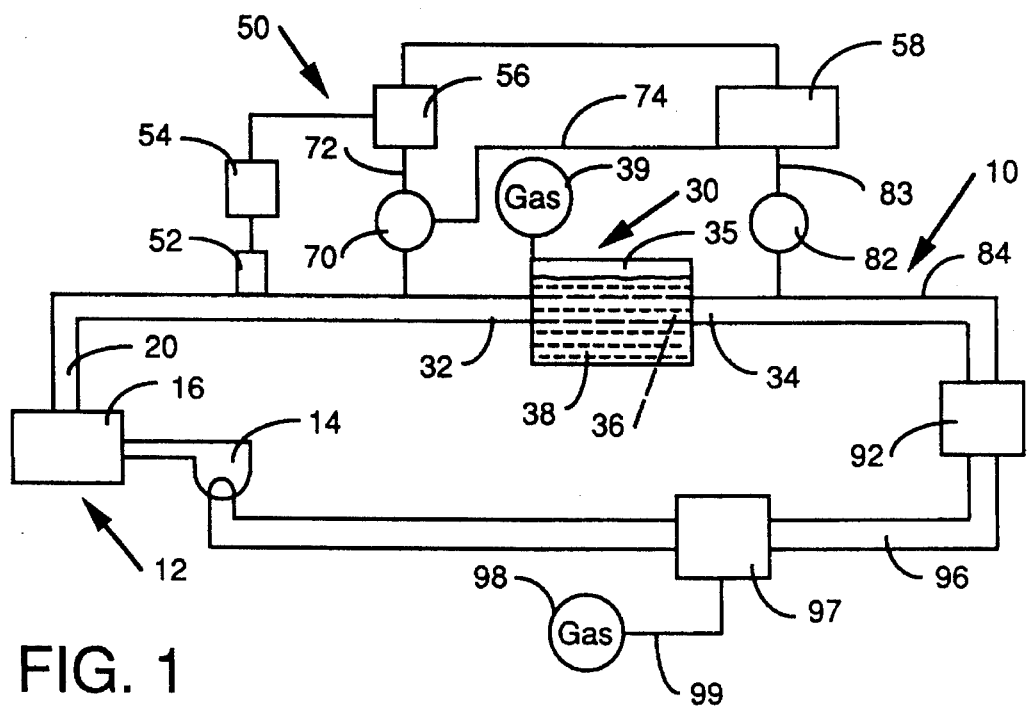
FIG. 1 is a schematic drawing of the fluid delivery apparatus of the invention.

Referring to FIG. 1, a schematic diagram of fluid delivery apparatus 10 is shown. The apparatus 10 has a fluid supply means 12 that includes a pump 14 and a regulator 16. A suitable pump 14 is a centrifugal pump sold under the trade designation Biomedicus 520D made by Biomedicus Corporation of Minneapolis, Minn. The regulator 16 can be a pressure regulator sold under the trade designation P50 made by Watts Regulator Company of Andover, Mass. Fluid, referred to as perfusate, is forced from the fluid supply means 12 into tubing 20. The perfusate used in this apparatus 10 is a tissue culture medium such as that sold under the trade name Media 199 made by Sigma Chemical Company of St. Louis, Mo.

The perfusate flows from the fluid supply means 12 via tubing 20 into a chamber 30. The chamber 30 has an inlet port 32 and a outlet port 34. The chamber 30 defines an enclosed space 35 in which a conduit, such as a portion of a human saphenous vein 36 is disposed. The saphenous vein 36 shown in FIG. 1 is bathed in a normothermic supplemented cell culture medium 38 such as that sold under the trade designation Media 199 by Sigma Chemical Company of St. Louis, Mo. The proper homeostatic environment for the cell culture medium 38 is maintained by a first gas supply source 39 that supplies a mixture of 95% air and 5% carbon dioxide to the chamber 30. The cell culture medium 38 is maintained at about 36.5° C. to 37.5° C.

In accordance with the invention, before reaching the chamber 30, the fluid pressure of the perfusate is modulated by modulating means 50 to create a desired pressure waveform. In the embodiment shown in FIG. 1, it is desired to circulate a fluid having a pressure waveform that mimics any of the blood pressure waveforms present throughout the human body. In this way, the conduit may be exposed to the same pulsatile fluid pressures and flows that are present in the human circulatory system.

Figure 2:
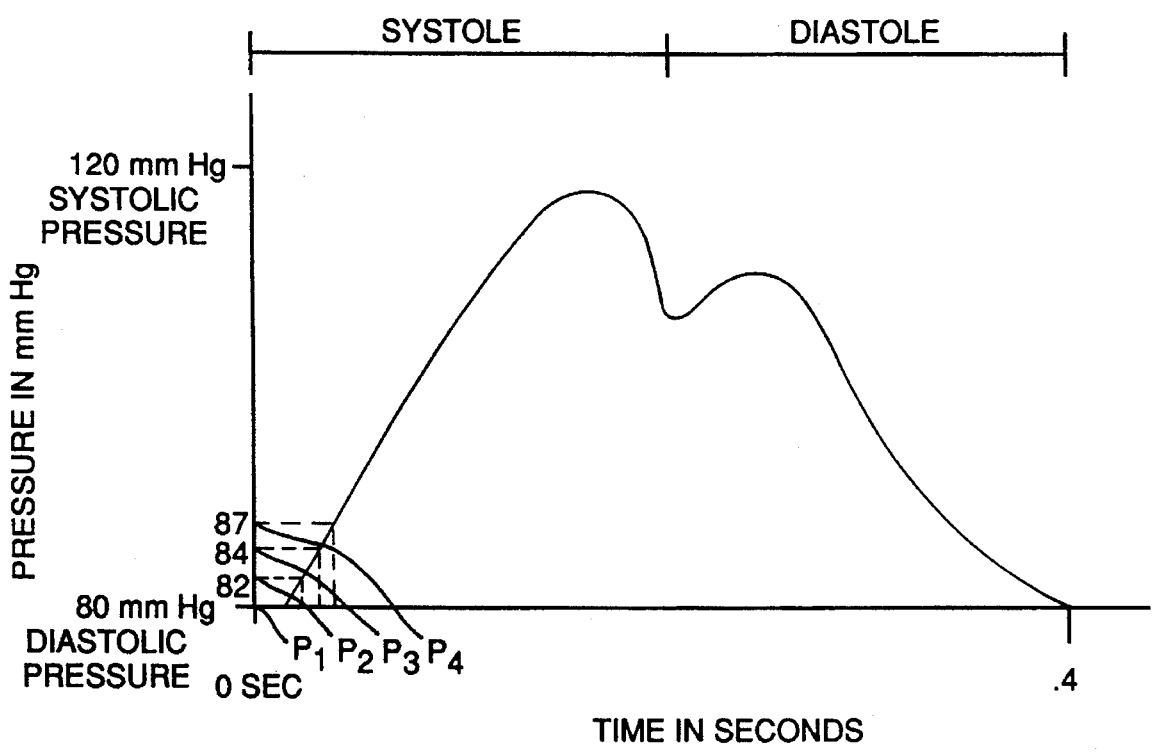
FIG. 2 is a graph showing the pressure waveform of human blood pressure.
Figure 3:
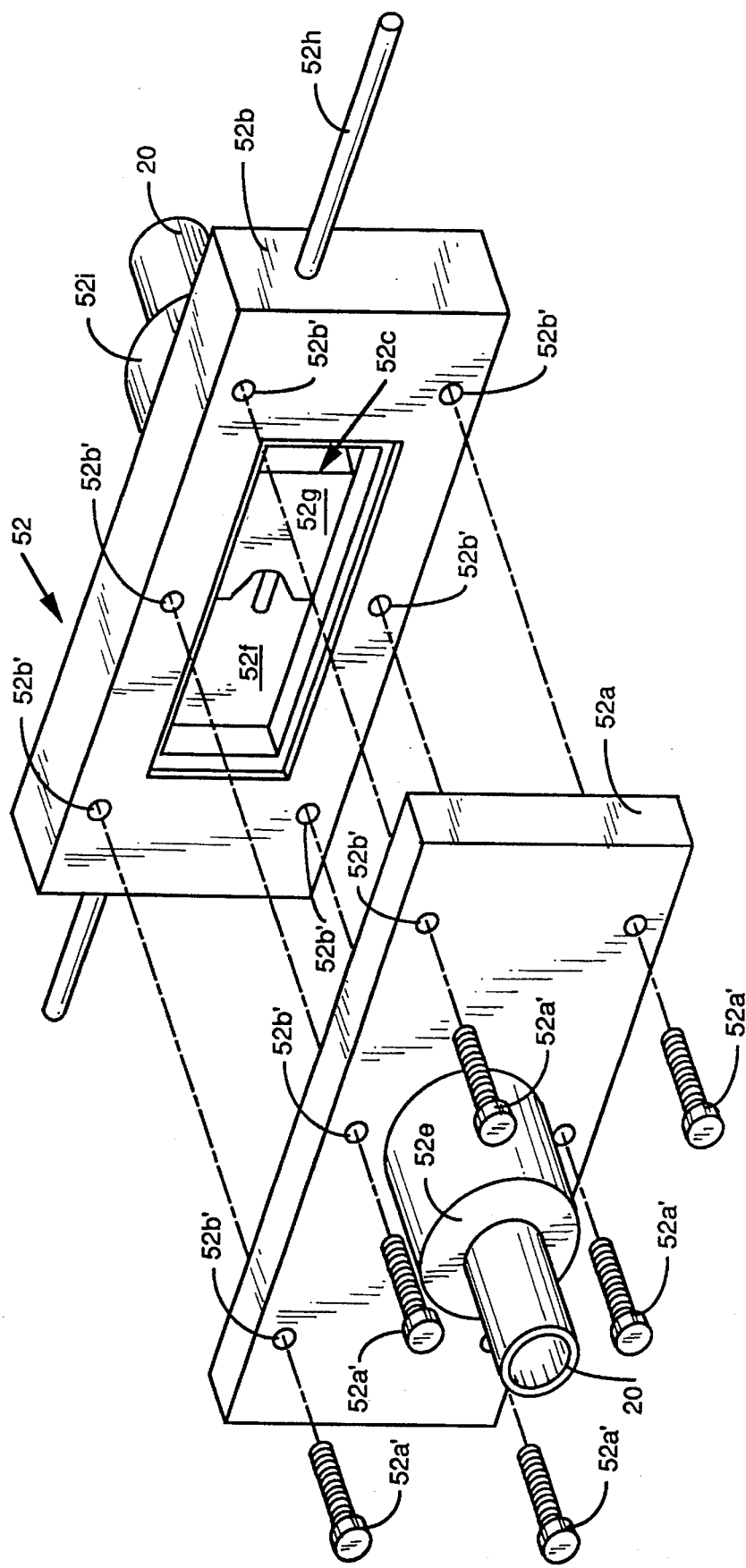
FIG. 3 is an exploded perspective view of the gate valve of the invention.

Referring now to FIG. 2, the pressure waveform of blood through the human circulatory system is graphically represented. Assuming a heart rate of one beat every one second, the blood pressure starts out at 80 mm Hg and then rises to a peak of 120 mm Hg. This portion of the curve is termed "systole" or when the heart is working. The maximum pressure is called the "systolic pressure" and in the pressure waveform of FIG. 2, occurs at 120 mm Hg.

The pressure drops rapidly and, characteristically, rises briefly, signalling the end of systole, and then falls again to its original lowest pressure, called "diastolic pressure". The diastolic pressure for the waveform of FIG. 2 is 80 mm Hg.

Thus, the "blood pressure reading" for the waveform of FIG. 2 is 120 mm Hg systolic pressure and 80 mm Hg diastolic pressure. More familiarly, the blood pressure reading would be termed "120 over 80", or a normal blood pressure reading for an adult human. Given a heart rate of sixty beats per minute, one beat occurs approximately over a time span of 0.4 seconds. The heart then rests in diastole for 0.6 seconds and then the cycle begins again, thus one cycle lasts 1.0 second.

The goal of the modulating means 50 is to reproduce, as closely as possible, the complex pressure waveform of a human blood pressure waveform. This is accomplished by modulating the fluid pressure emanating from the fluid supply means 12 into a fluid having a desired pressure waveform, such as that shown in FIG. 2. It will be appreciated that the pressure modulating means 50 can be manipulated to produce other pressure waveforms such as different blood pressure waveforms (such as "140 over 90" blood pressures or faster heart rates). In this way, the apparatus can be used to mimic several different types of blood pressure waveforms that occur in humans or animals in both healthy and disease states.

In accordance with the invention, the fluid pressure of the perfusate delivered to the vessel chamber 30 is controlled by the modulation means designated generally by the reference character 50. Before reaching the vessel chamber 30 from the fluid supply means 12, a linear gate valve 52 is translated back and forth across the fluid flow to create the desired fluid pressure to be introduced to the inlet port 32 of the vessel chamber 30. The linear gate valve 52 is moved by a linear motor 54 that is controlled by a programmable linear motion controller 56. A suitable programmable motion controller is sold under the trade designation DMC-720 by Galil Motion Control, Inc. of Sunnyvale, Calif. A suitable brushless linear motor is sold under the trade designation T200-4B by Trilogy Systems, Inc. of Webster, Tex.

The linear gate valve 52 is shown in more detail in FIGS. 3–6. The linear gate valve 52 consists of a two-piece housing 52a and 52b joined by a plurality of screws 52a' which are adapted to be threadedly engaged into holes 52b' which contains the gate valve assembly 52c. Mounted on housing 52a is an inlet port 52e which is adapted to receive tubing 20 from the fluid supply means 12. The fluid flows through inlet port 52e into the gate valve assembly 52c which consists of a fixed plate 52f and a movable plate 52g. Movable plate 52g is adapted for translational movement in the gate valve assembly 52c as will be explained below with respect to FIGS. 4–6. This is accomplished by a rod 52h which is, in turn, connected to the brushless linear motor 54 controlled by the motion controller 56. The fluid exits the gate valve assembly through outlet port 52i which is adapted to be connected to tubing 20 which leads to the chamber 30.

Figure 4:
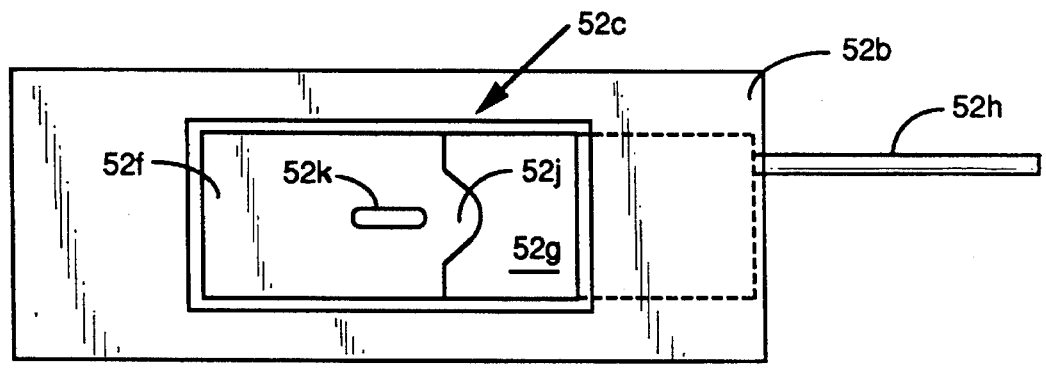
FIG. 4 is a vertical section of the gate valve showing it completely open.
Figure 5:
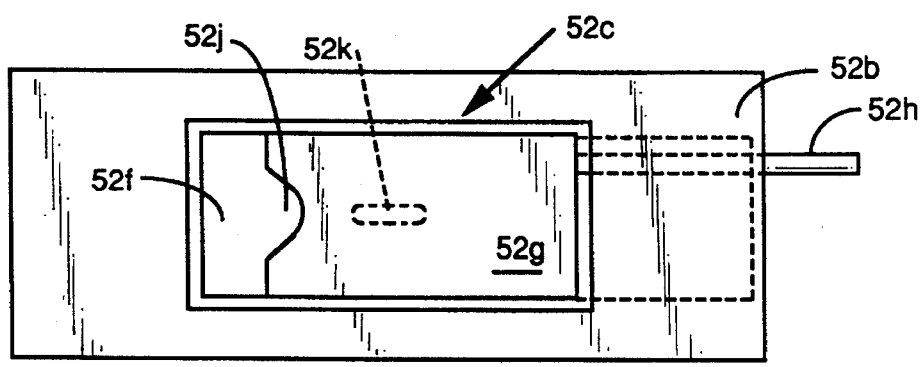
FIG. 5 is a vertical section of the gate valve showing it completely closed.
Figure 6:
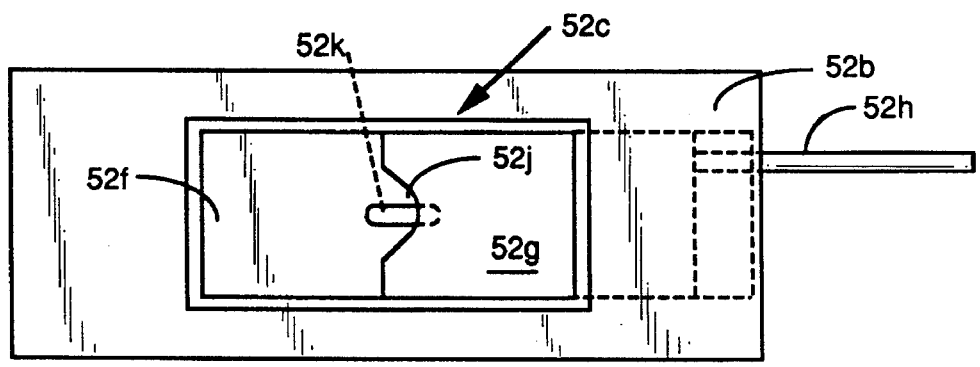
FIG. 6 is a vertical section of the gate valve showing it partially open.

Referring now to FIGS. 4–6, it will be seen that the movable plate 52g defines a semi-circular cut-out area 52j and fixed plate 52f defines a slotted opening 52k. The movable plate 52g in FIG. 4 is shown in the "totally open position". In this position, fluid flowing into the gate valve 52 is not modulated and flows fully through slotted opening 52k into outlet port 52i and then to tubing 20. Thus, the pressure of the fluid entering the inlet port 52e is approximately equal to the pressure of the fluid exiting the outlet port 52i.

It will be appreciated, however, that non-modulated flow can be obtained without positioning the movable plate 52g in the position shown in FIG. 4. Substantially non-modulated flow, for example, can be obtained even if the movable plate 52g blocks a small part of the fluid flowing through the slotted opening 52k.

Referring now to FIG. 5, the movable plate 52g is translated to the left, so that the movable plate 52g completely blocks slotted opening 52k. This is the "totally closed position" in which no fluid flows into the slotted opening 52k and through the outlet port 52i into tubing 20. Finally, referring to FIG. 6, the partially opened/closed position of the movable plate 52g is shown. In this case, the pressure of the fluid is modulated so that the pressure of the fluid out of the gate valve 52 and eventually to chamber 30 is less than the pressure of the fluid into the gate valve 52. It will be appreciated that controlling the movement of movable plate 52g modulates the pressure of the fluid out of the gate valve 52.

The linear gate valve 52 is just one embodiment of an apparatus that restricts fluid delivery to the chamber 30 and the invention is not limited to this particular mechanical fluid delivery restriction means. Other apparatus can include an occlusion device which mechanically occludes the tubing 20 itself so as to restrict fluid delivery to the chamber 30. As used herein the expression "restriction" or "restricting" means altering flow and modulating the pressure of a fluid such as by using a valve or physical occlusion of tubing.

Referring back to FIG. 1, the movement of the linear gate valve 52 by the linear motor 54 is controlled by the motion controller 56. The motion controller 56, in turn, is connected to a microprocessor 58. A suitable microprocessor 58 is sold under the trade designation Gateway 2000 386SX PC by Gateway of North Sioux City, N.Dak. The pressure of the fluid after passing the linear gate valve 52 is measured by pressure transducer 70. As will be explained in further detail with respect to FIG. 7, the pressure transducer 70 feeds back the pressure reading to the motion controller 56 through line 72 and based on this feedback the motion of the linear gate valve 52 is controlled. A line 74 is also provided from the pressure transducer 70 to the microprocessor. 58 in order to record in the microprocessor 58 the pressure readings.

After the perfusate flows through the conduit 36, it exits the outlet port 34 of the chamber 30 through tubing 84. The exit fluid pressure is monitored by pressure transducer 82, with the pressure readings being recorded in the microprocessor 58 via line 83. The perfusate then flows into a valve 92. The perfusate then exits the valve 92 via tubing 96 and then flows into collection chamber 97. At this point a 95% air/5% carbon dioxide air mixture is introduced into the perfusate by gas source 98 through line 99. This air mixture maintains the required parameters (pH, $PCO_2$, $PO_2$) of the perfusate in order for the perfusate to biochemically mimic human blood.

The baseline pressure, defined as the pressure with the gate valve 52 in the completely open position as shown in FIG. 4, is controlled by the pump 14, regulator 16 and the valve 92. For example, it may be desired to create a flow of 100 ml/min which is the mean arterial flow in a coronary artery. It will be appreciated that by controlling the pump 14 and regulator 16, in concert with the valve 92, that a sufficient baseline pressure and flow will be produced. The baseline pressure must be greater than the highest pressure desired in the waveform. For example, if the highest pressure in the waveform is 120 mm Hg it is desired that the baseline pressure be at least 130 mm Hg and preferably more.

In general, the apparatus 10 functions as follows. The microprocessor 58 includes an output device, such as a computer screen, which asks the user to first select a desired pressure waveform, such as that shown in FIG. 2. To select a desired pressure waveform, a choice of ten representative analog pressure waveforms from the human circulatory tree are graphically displayed. These waveforms are derived from the work of D. A. McDonald, *Blood Flow In Arteries*, 1960, pp. 234–237, which is incorporated herein by reference. To customize these curves, the user must also specify peak (systolic) pressure and trial (diastolic) pressure, frequency of the pressure cycle (from 3 to 0.1 second$^{-1}$) and duration or cycle time of the experiment which can be up to 14 days. In addition, the "tolerance" of the waveform is set. This will be explained hereinbelow. Once these selections are input into the microprocessor 58, the microprocessor 58 digitizes the chosen analog curve. Preferably, a digitized point is generated every 4 milliseconds to insure accurate waveform representation (according to the Nyquist theorem). The number of digitized points may be any binary number from $2^1$ to $2^{10}$. More complex pressure waveforms require more digitized points for accurate representation. For the vast majority of physiologic pressure waveforms, $2^7=128$ digitized points have empirically proven sufficient. Thus, each pressure waveform includes one hundred and twenty-eight digitized data pressure points equally spaced with regard to time. Referring to FIG. 2, if this pressure waveform is selected, the microprocessor will digitize point $P_1$ corresponding to a pressure of 80 mm Hg, point $P_2$ corresponding to a pressure of 82 mm Hg, point $P_3$ corresponding to a pressure of 84 mm Hg, and point $P_4$ corresponding to a pressure of 87 mm Hg and so on until the pressure waveform is digitized into one hundred and twenty-eight pressure points equally spaced in time. The digitized data is then downloaded to the motion controller 56.

Once the customized, desired pressure waveform is entered into the microprocessor 58 and downloaded to the motion controller 56, the motion controller 56 executes the motion controller computer program which is stored in the microprocessor 58 and which is also downloaded to the motion controller 56 along with the digitized desired pressure waveform. The motion controller 56 begins execution of the pressure generation program by requesting information about the movement of the gate valve 52. The gate valve 52 is closed until the fluid flow is just obstructed resulting in a zero pressure reading being registered by the pressure transducer 70. After this, the gate valve 52 is opened gradually until the pressure reaches a maximum. The maximum is determined at the position when further opening movement of the gate valve does not create a further rise in pressure. With the maximum and minimum positions determined, the valve is moved to the "starting position" which is defined as the position where the diastolic pressure (in the case of FIG. 2, 80 mm Hg) is achieved.

Next, the pressure waveform is constructed point-by-point. In order to match the measured pressure array with the desired pressure array, an iterative process is begun. The motion controller 56 initiates movement of the gate valve 52. The resultant pressure is measured by pressure transducer 70 and compared to the first digitized pressure point. A correction algorithm is applied until the measured error falls within an acceptable tolerance.

Once a gate valve 52 position is determined which generates a measured pressure within the tolerance of the first digitized pressure point of the selected pressure waveform, the system stores this in memory and moves on to identify the second gate valve position corresponding to a measured pressure within the tolerance of the second desired digitized point. Thus, through this iterative process a complete waveform is created. Once this is done, the program instructs the gate valve 52 to create the pressure waveform over and over again for the entire duration of the experiment.

Figure 7:
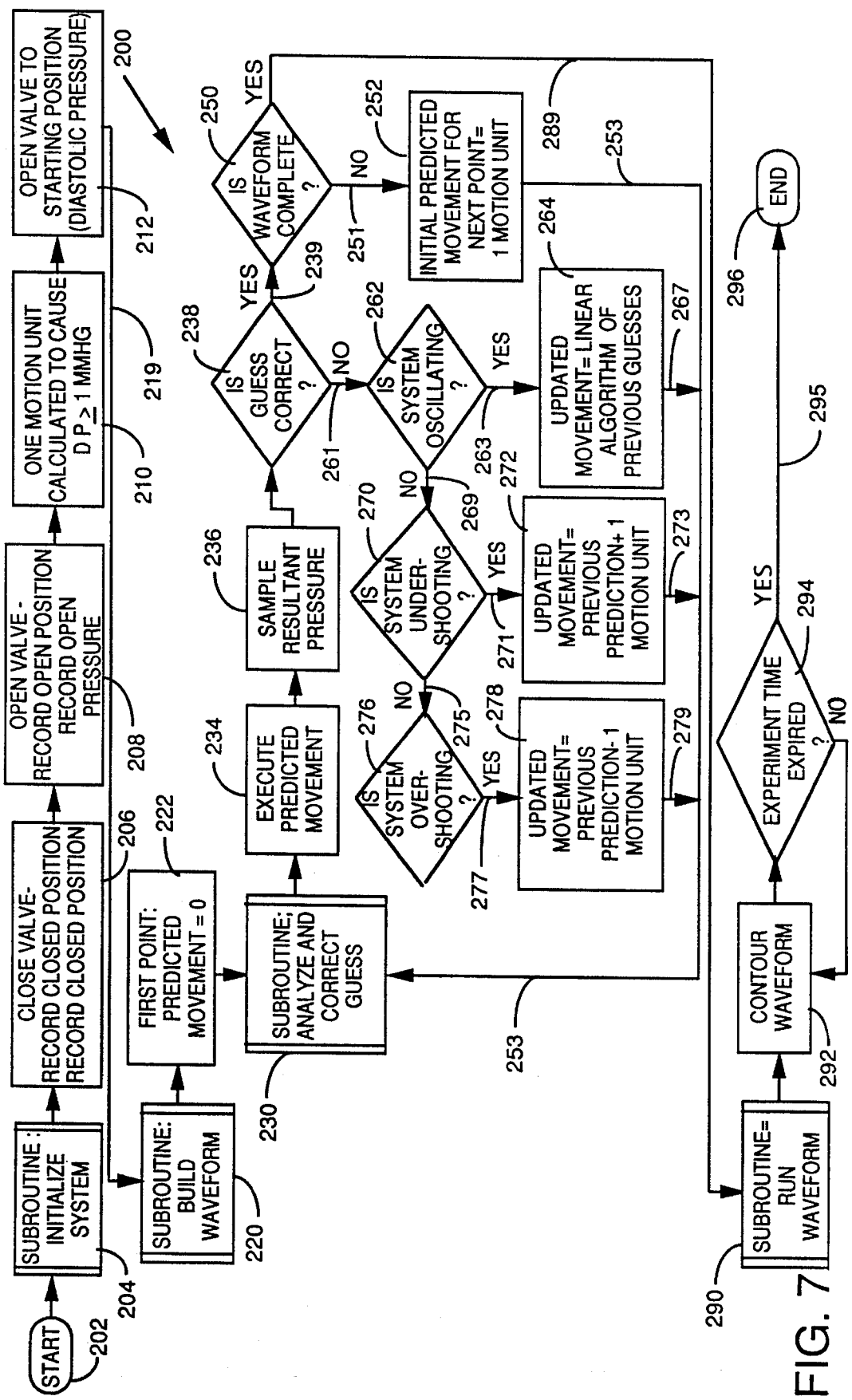
FIG. 7 is a flow chart of the motion controller computer program.

Referring now to FIG. 7, the motion controller program 200 is shown in flow chart form. It will be appreciated that one skilled in the art can write software code that can implement the algorithm shown in the flow chart of FIG. 7. The program 200 starts at start block 202 and then proceeds to the INITIALIZE SYSTEM subroutine 204. The user manually closes gate valve 52 by use of the linear motor 54 and enters via the microprocessor 58 a command which causes the position of the gate valve 52 and the resultant pressure of the fluid after passing the gate valve 52 to be recorded in the program 200 at block 206. After this, the user slowly opens the gate valve 52 by use of the linear motor 54. The user keeps opening the gate valve 52 while the pressure increases and stops opening the gate valve 52 just after the pressure stops increasing. The user enters via the microprocessor 58 a command which causes the position of the gate valve 52 and the resultant pressure of the fluid passing the gate valve 52 to be recorded in the program at block 208. The maximum and minimum pressure gate valve 52 positions determined in blocks 206 and 208 are used as limits for the system.

The program 200 then determines the value of a "motion unit" at block 210. A motion unit is defined as a discrete quantity of motion which produces pressure changes of at least 1 mm Hg. Gate valve 52, for example, may travel a total of 3 mm in going from a completely closed to a completely open position. The pressure range over this distance is 0 mm Hg (when the valve is completely closed) to at least systolic pressure=120 mm Hg (when the valve is completely open). Thus, one motion unit would be:

$$1 \text{ Motion Unit} \geq 1 \text{ mmHg} * \frac{3 \text{ mm}}{120 \text{ mmHg} - 0 \text{ mmHg}} = 0.025 \text{ mm}$$

One motion unit can thus be defined at 0.03 mm. This value is used below in the BUILD WAVEFORM subroutine which will be discussed further hereinbelow.

The program 200 then moves to block 212 where the user manually moves the gate valve 52 by use of the linear motor to the position where the pressure produced is equal to the diastolic pressure of the desired pressure waveform. Referring to the pressure waveform of FIG. 2, the diastolic pressure is 80 mm Hg. This is deemed to be the starting point for formation of the desired pressure waveform. Once the starting position of the gate valve 52 has been determined, the program 200 moves via line 219 to the BUILD WAVEFORM subroutine 220.

As was discussed generally above, the motion controller program involves an "iterative shooting" concept wherein guesses are taken for the position of the gate valve to create a pressure point from the desired pressure waveform. As was discussed above, the desired pressure waveform is chosen by the user based on a display on the microprocessor screen of ten different representative waveforms and is then adjusted by specifying the frequency (beats per second) and amplitude (difference between diastolic and systolic pressure). The desired pressure waveform as selected and adjusted by the user is digitized by the microprocessor and downloaded into the motion controller computer program. The digitization is based on representing the pressure waveform as a series of one hundred and twenty-eight discrete points equally separated in time. The operation of the program 200 will be discussed with reference to a desired pressure waveform as is shown in FIG. 2.

Referring back to FIG. 2, the desired pressure waveform has a first pressure point $P_1$ (the starting point) which is equal to the diastolic pressure of 80 mm Hg. The second pressure point $P_2$ is equal to 82 mm Hg, the third pressure point $P_3$ is equal to 84 mm Hg, the fourth pressure point $P_4$ is equal to 87 mm Hg and so on until the one hundred and twenty-eighth digitized pressure point $P_{128}$ which is equal to 80 mm Hg. We have found that dividing the pressure waveform into a series of one hundred and twenty-eight discrete pressure points equally spaced in time gives a very accurate representation of the entire pressure waveform.

The BUILD WAVEFORM subroutine 220 determines the gate valve 52 position for each of the one hundred and twenty-eight pressure points that make up the pressure waveform. This is done by using the digitized and downloaded pressure waveform (such as that shown in FIG. 2) as a guide. That is, the BUILD WAVEFORM subroutine creates the desired pressure waveform by a pressure point to pressure point comparison with the digitized and downloaded pressure waveform. For example, point $P_1$ of FIG. 2 represents a certain gate valve 52 position that creates a pressure of 80 mm Hg, point $P_2$ represents a certain gate valve 52 position that creates a pressure of 82 mm Hg and so forth to point $P_{128}$. The BUILD WAVEFORM subroutine determines the gate valve 52 position for each point, $P_1$ to $P_{128}$, in order to construct the desired pressure waveform.

The BUILD WAVEFORM subroutine 220 first moves to block 222 wherein the position of the gate valve 52 to create the first point of the desired pressure waveform is determined. As the first point of the desired pressure waveform is also the diastolic pressure (see FIG. 2), the gate valve 52 is already in the correct position because it was set in block 212 in the INITIALIZE SYSTEM subroutine. Thus, the "predicted movement" of the gate valve 52 in the case of the first pressure point of the desired pressure waveform is zero. By "movement" it is meant linear movement of the linear gate valve 52 across the fluid as was explained in FIGS. 3–6.

After this, the program 200 moves to the ANALYZE AND CORRECT GUESS subroutine 230. The first thing that occurs in this subroutine 230 is for the program 200 to instruct the gate valve 52 to move the predicted movement. As the predicted movement for the first point is zero as was discussed above with respect to block 222, the subroutine 230 moves to block 234 wherein the program instructs the gate valve 52 to execute the predicted movement, which in this case is zero. With that done, the program 200 moves to block 236 wherein the resultant pressure of the fluid is sampled by pressure transducer 70 (see FIG. 1). Because the predicted movement for the first point is zero, the resultant pressure is equal to the starting pressure of 80 mm Hg, as set in block 212.

In block 238, the resultant pressure is compared to the pressure point $P_1$ of the digitized and downloaded pressure waveform. Returning to FIG. 2, the pressure point $P_1$ has a value of 80 mm Hg. Assuming the resultant pressure is 80 mm Hg, the subroutine 230 will indicate that the guess is correct, and will continue via line 239 to decision block 250. At decision block 250, it is determined whether or not the waveform is complete. Obviously, with one hundred and twenty-eight pressure points to determine, the pressure waveform after determining the first pressure point is not complete and thus goes to block 252 via line 251.

At block 252, the program 200 sets the predicted movement for the next pressure point to be determined in the desired pressure waveform (i.e., the pressure point that corresponds to pressure point $P_2$ of the digitized and downloaded pressure waveform) equal to one motion unit. The movement of the gate valve 52 corresponding to one motion unit was discussed at block 210. In this case, the movement is plus one motion unit. The ANALYZE AND CORRECT GUESS subroutine 230 then returns to block 230 via line 253, and the process of executing the predicted movement (block 234) Sampling the resultant pressure (block 236) and comparing the resultant pressure to the next point in the digitized and downloaded pressure waveform (decision block 238) is performed. If the guess is correct, the subroutine continues as was discussed above, with the third point next being determined.

A "correct guess" consists of a resultant pressure which falls within a predetermined tolerance limit. The tolerance limit is set by the user at the outset of the process and is stored in the microprocessor 58. In block 238 the resultant pressure is compared to the tolerable range of acceptable pressures. For example, if the tolerance limit is 0.5 mm Hg, and the digitized and downloaded pressure point that the resultant pressure is compared to is 82 mm Hg, this means that any resultant pressure falling in the range of 81.5 mm Hg to 82.5 mm Hg is "correct". Obviously, any resultant pressure falling outside this range is "incorrect". We have found that a tolerance limit of 0.5 mm Hg is an acceptable tolerance for constructing the desired pressure waveform.

If the guess made for the second point is incorrect, the subroutine proceeds via line 261 to block 262 in which it is determined whether the system is oscillating. Oscillation will be explained further hereinbelow. For present purposes, assume the system is not in oscillation, and thus the subroutine proceeds via line 269 to decision block 270 which determines whether the system is "undershooting", i.e., whether the resultant pressure is lower than the desired pressure by the predetermined tolerance.

For example, referring to FIG. 2, if the system's resultant pressure was 81 mm Hg and point $P_2$ is 82 mm Hg, this would be an incorrect guess and would mean that the gate valve 52 was not opened wide enough thus causing an "undershooting" of the pressure. If this is the case, the subroutine via line 271 goes to block 272 in which the predicted movement is changed so that the new "updated" predicted movement is one motion unit more than the "old" predicted movement. The new "updated" movement is sent via line 273 into line 253 and the process of executing the new predicted movement (block 234), sampling the resultant pressure (block 236) and comparing it to the digitized and downloaded pressure point $P_2$ (decision block 238) is done again.

If the system is not "undershooting", the subroutine proceeds via line 275 to block 276 which determines whether the system is "overshooting", i.e., whether the resultant pressure is higher than the desired pressure range. For example, if the system's resultant pressure was 83 mm Hg and point $P_2$ is 82 mm Hg this would be an incorrect guess and would mean that the gate valve closed too much thus causing an "overshooting" of the pressure. If this is the case, the subroutine via line 277 goes to block 278 in which the predicted movement is changed so that the new "updated" predicted movement is one motion unit less than the "old" predicted movement. The updated predicted movement is sent via line 279 into line 253 and the process of executing the new predicted movement (block 234) sampling the resultant pressure (block 236) and comparing it to the digitized and downloaded pressure point P2 (decision block 238) is done again.

It will be appreciated that the process continues until the resultant pressure is within the specified tolerance. However, sometimes the system will go into "oscillation". By "oscillation" it is meant that there has been an "undershooting" incorrect guess followed by an "overshooting" incorrect guess. If the system is in oscillation, block 262 will lead via line 263 to block 264 where a linear algorithm is applied to the previous two guesses (which, by definition is one "undershooting" guess and one "overshooting" guess) in order to determine an updated movement.

As an example, and referring back to FIG. 2 and point $P_2$, assume the subroutine made a first "undershooting" guess of 81 mm Hg and then a second "overshooting" guess of 84 mm Hg for point $P_2$ (whose tolerance range is 81.5 to 82.5 mm Hg). This means the system is in oscillation, which will lead the subroutine to block 264. Assume again that in trying to find $P_2$=82 mm Hg, a first guess of three motion units resulted in a pressure of 81 mm Hg and a subsequent guess of four motion units resulted in a pressure of 84 mm Hg. The program then employs a linear algorithm to predict the proper position as follows (where POS=position and PRES=pressure):

$$POS_{next} = POS_{undershoot} + (POS_{overshoot} - POS_{undershoot}) * \frac{[PRES_{desired} - PRES_{undershoot}]}{[PRES_{overshoot} - PRES_{undershoot}]}$$

Substituting in this equation the specific numbers from above leads to the following (where MU=motion units):

$$POS_{next} = 3\,MU + [4\,MU - 3\,MU] * \frac{[83\,\text{mmHg} - 81\,\text{mmHg}]}{[84\,\text{mmHg} - 81\,\text{mmHg}]} = 3 1/3\,MU$$

Converting this to absolute motion (using the definition of a motion unit from box 210 above):

$$POS_{next} = 3 1/3 * \frac{0.03\,\text{mm}}{1\,MU} = 0.1\,\text{mm}$$

This new updated movement will be sent via line 267 to line 253 and back to the beginning of the BUILD WAVEFORM subroutine.

Once the position of the gate valve 52 related to the second point is in the range of acceptable pressures for point $P_2$ of the digitized and downloaded pressure waveform, the subroutine proceeds via line 239 to the decision block 250 in which it is determined whether the waveform is complete. Since the waveform has done only two of the one hundred and twenty-eight points, it is obviously not complete and thus the program proceeds via line 251 to block 252 and the initial predicted movement for the third point $P_3$ is determined. It will be appreciated that the above process continues for the third point $P_3$ and then the program moves to the fourth point $P_4$ and so on until all one hundred and twenty-eight points are determined. Once that happens the ANALYZE AND CORRECT GUESS subroutine comes to an end and the program 200 proceeds via line 289 to the RUN WAVEFORM subroutine 290.

The RUN WAVEFORM subroutine 290 consists of contouring the waveform in block 292 and running the waveform through the system until the experiment time has expired (block 294). The experiment time is set by the user and can be any integer from 1 to infinity (a cycle being one "heartbeat" as is shown in FIG. 2). Once the number of cycles for the experiment have been completed, the program via line 295 goes to an end 296.

In an alternate motion controller program to that shown in FIG. 7, the desired pressure waveform is converted to a specific opening and closing pattern of the gate valve 52 by approximating the transfer function of the system with a linear function. To implement this scheme, the desired pressure waveform shown in FIG. 2 is changed from absolute to relative pressure by subtracting the offset component (the diastolic pressure) from each digitized point. For example, the first four digitized points discussed earlier were 80 mm Hg, 82 mm Hg, 84 mm Hg, and 87 mm Hg. Subtracting the diastolic pressure of 80 mm Hg, the corresponding resultant array is 0 mm Hg, 2 mm Hg, 4 mm Hg, and 7 mm Hg. After this, the relative, digitized pressure array (as a function of time), henceforth referred to as P'(t), can be converted to valve motion, x(t), through the following linear approximation:

$$x(t)=c*P'(t)$$

The constant, c, is a scaling factor determined in the following manner. The valve is closed to a position where the diastolic pressure, 80 mm Hg, is achieved, and this position is recorded. In a similar manner, the valve is opened to a position where the systolic pressure, 120 mm Hg, is achieved, and this position recorded. The scaling factor is then calculated as:

$$c = \frac{[\text{ValvePosition}_{120\,mmHg} - \text{ValvePosition}_{80\,mmHg}]}{[120\,\text{mmHg} - 80\,\text{mmHg}]}$$

For example, if the diastolic pressure occurs at a valve position of 1.1 mm and the systolic pressure occurs at a valve position of 2.7 mm, then:

$$c = \frac{[2.7\,\text{mm} - 1.1\,\text{mm}]}{[120\,\text{mmHg} - 80\,\text{mmHg}]} = .04\,\frac{\text{mm}}{\text{mmHg}}$$

Using this constant as the linear transfer function, each position corresponding to relative pressure is determined. The gate valve 52 is then set at the diastolic position (80 mm Hg), and the valve is moved according to the calculated x(t).

Furthermore, the user can test the accuracy of the actual pressures produced by running the system with the microprocessor recording the resultant pressures. The resultant pressures are plotted on a graph which is displayed to the user. The user can use this graph to make adjustments to the gate valve position for any of the one hundred and twenty-eight digitized pressure point.

The method of the invention includes providing a chamber to hold the conduit and a fluid supply means for supplying fluid to the conduit and modulating the pressure of the fluid before the fluid is delivered to the conduit so that the fluid has a desired pressure. The modulating step comprises at least partially restricting the delivery of the fluid to the conduit, measuring the pressure of the fluid prior to the fluid entering the conduit, comparing the measured pressure of the fluid flow to the desired pressure and adjusting the restriction of the delivery of the fluid to the conduit based on the comparison.

It will be appreciated that a fluid delivery apparatus and associated method have been disclosed which provide a predetermined pressure waveform to a conduit. The apparatus and method are especially useful for (i) conditioning human saphenous veins which are used in coronary bypass surgical procedures and (ii) for testing the response of chemical mediators (commonly referred to as drugs) on vascular tissues.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A fluid delivery apparatus comprising:

a chamber for holding a conduit;

fluid supply means for delivering to said conduit a fluid having a pressure;

means for modulating said fluid pressure before said fluid is delivered to said conduit to produce a desired fluid pressure for delivery to said conduit;

said modulating means including:

mechanical means for at least partially restricting said delivery of said fluid to said conduit;

means for measuring the pressure of said fluid prior to said fluid being delivered to said conduit;

means for adjusting said mechanical means based on a comparison of said pressure of said fluid as measured by said measuring means and said desired fluid pressure, said adjusting means includes a motion controller means; and said mechanical means includes (i) a linear motor electrically connected to said controller means and (ii) gate valve means in operative association with said linear motor.

2. The apparatus of claim 1, wherein said adjusting means includes a microprocessor.

3. The apparatus of claim 2, wherein said microprocessor (i) stores a plurality of pressure waveforms from which can be selected said desired pressure waveform and (ii) stores a motion controller computer program.

4. The apparatus of claim 3, wherein said microprocessor (i) receives input from a user to modify said selected desired pressure waveform and (ii) modifies said selected desired pressure waveform based on said user provided information.

5. The apparatus of claim 3, wherein said motion controller means (i) receives said desired pressure waveform and said computer program instructions from said microprocessor and (ii) causes said mechanical means to move based on said desired pressure waveform and said computer program instructions.

6. The apparatus of claim 1, wherein said gate valve means includes (i) a housing defining a passageway in which said fluid can flow and (ii) a gate movably disposed in said passageway, whereby movement of said gate modulates said fluid pressure.

7. The apparatus of claim 1, wherein said conduit is a vascular tissue; and said chamber defines an enclosed space, said enclosed space containing a cell culture media for bathing said vascular tissue.

8. The apparatus of claim 1, including collection device means downstream of said chamber for receiving said fluid after said fluid has flowed through said conduit and delivering said fluid back to said fluid supply means for circulation to said conduit.

9. A fluid delivery apparatus comprising:

a chamber for holding a conduit;

fluid supply means for delivering to said conduit a fluid having a pressure;

means for modulating said fluid pressure before said fluid is delivered to said conduit to produce a desired fluid pressure for delivery to said conduit;

said modulating means including:

mechanical means for at least partially restricting said delivery of said fluid to said conduit;

means for measuring the pressure of said fluid prior to said fluid being delivered to said conduit;

means for adjusting said mechanical means based on a comparison of said pressure of said fluid as measured by said measuring means and said desired fluid pressure;

collection device means downstream of said chamber for receiving said fluid after said fluid has flowed through said conduit and delivering said fluid back to said fluid supply means for circulation to said conduit; and gas supply means connected to said collection device for supplying a gas mixture to said fluid disposed in said collection device.

10. A method of delivering a fluid having a desired pressure to a conduit, said method comprising:

providing (1) a chamber to hold said conduit and (ii) fluid supply means for delivering said fluid to said conduit;

modulating the pressure of said fluid before said fluid is delivered to said conduit so that said fluid has said desired pressure;

said modulating step comprising:

at least partially restricting said delivery of said fluid to said conduit;

measuring the pressure of said fluid prior to said fluid entering into said conduit;

comparing said measured fluid pressure to said desired pressure; and adjusting said restriction of said delivery of said fluid to said conduit based on said comparison;

employing as said conduit vascular tissue from a human or an animal; and employing said method to condition a human saphenous vein for use in a bypass surgical procedure.

11. A method of delivering a fluid having a desired pressure to a conduit, said method comprising:

providing (i) a chamber to hold said conduit and (ii) fluid supply means for delivering said fluid to said conduit;

modulating the pressure of said fluid before said fluid is delivered to said conduit so that said fluid has said desired pressure;

said modulating step comprising:

at least partially restricting said delivery of said fluid to said conduit;

measuring the pressure of said fluid prior to said fluid entering into said conduit;

comparing said measured fluid pressure to said desired pressure; and adjusting said restriction of said delivery of said fluid to said conduit based on said comparison;

employing as said conduit vascular tissue from a human or an animal; and introducing into said fluid a pharmaceutical compound, whereby the effect of said compound on said vascular tissue can be determined.

12. The method of claim 11, including employing as said desired pressure a pressure waveform having a plurality of discrete pressure data points; and repeating said modulating step for each of said discrete pressure data points.

13. The method of claim 12, including providing modulating means to modulate said pressure of said fluid, said modulating means including (i) mechanical means for at least partially restricting said delivery of said fluid to said conduit; (ii) means for measuring the pressure of said fluid prior to said fluid being delivered to said conduit; and (iii) means for adjusting said mechanical means based on a comparison of said pressure of said fluid as measured by said measuring means and said desired pressure;

employing as said adjusting means a microprocessor and motion controller means;

storing in said microprocessor means a plurality of pressure waveforms; and selecting one of said pressure waveforms as said desired pressure.

14. The method of claim 13, including storing in said microprocessor means a motion controller computer program; and adjusting said mechanical means based on said motion controller computer program.

15. The method of claim 14, including said selected pressure waveform having pressure waveform characteristics; and modifying said pressure waveform characteristics to obtain said desired pressure.

* * * * *

UNITED STATES PATENT AND TRADEMARK OFFICE
CERTIFICATE OF CORRECTION

PATENT NO. : 5,537,335
DATED : July 16, 1996
INVENTOR(S) : JAMES F. ANTAKI, ROBERT F. LABADIE and HARVEY S. BOROVETZ It is certified that error appears in the above-indentified patent and that said Letters Patent is hereby corrected as shown below:

Column 10, line 27, in the equation, "83 mmHg" should be --82 mmHg--.

Signed and Sealed this

Third Day of December, 1996

Attest:

BRUCE LEHMAN

*Attesting Officer*      *Commissioner of Patents and Trademarks*